(12) United States Patent
Chi et al.

(10) Patent No.: US 8,507,679 B2
(45) Date of Patent: Aug. 13, 2013

(54) HETEROLEPTIC, DUAL TRIDENTATE RU(II) COMPLEXES AS SENSITIZERS FOR DYE-SENSITIZED SOLAR CELLS

(75) Inventors: Yun Chi, Hsinchu (TW); Chun-Cheng Chou, Hsinchu (TW); Kuan-Lin Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 459 days.

(21) Appl. No.: 12/966,405

(22) Filed: Dec. 13, 2010

(65) Prior Publication Data

US 2012/0073660 A1    Mar. 29, 2012

(30) Foreign Application Priority Data

Sep. 28, 2010 (TW) ............................ 99132723 A

(51) Int. Cl.
*C07F 15/00* (2006.01)
*H01L 31/00* (2006.01)

(52) U.S. Cl.
USPC ............................... 546/2; 136/263; 136/252

(58) Field of Classification Search
USPC ...................... 546/2; 136/263, 252
See application file for complete search history.

(56) References Cited

U.S. PATENT DOCUMENTS

2010/0258175 A1*  10/2010  Chi et al. ................... 136/256

* cited by examiner

*Primary Examiner* — Charanjit Aulakh
(74) *Attorney, Agent, or Firm* — Muncy, Geissler, Olds & Lowe, PLLC

(57) ABSTRACT

Photosensitizers having a formula of $RuL_1L_2$ (1) are provided, wherein Ru is ruthenium; $L_1$ and $L_2$ are heterocyclic tridentate ligands. $L_1$ has a formula of (2), and $L_2$ has a formula of $G_1G_2G_3$ (3), wherein $G_1$ and $G_3$ are selected from the group consisting of formulae (4) to (7), and $G_2$ is selected from the group consisting of formulae (7) and (8). The above-mentioned photosensitizers are suitable to be used as sensitizers for fabrication of high efficiency dye-sensitized solar cells.

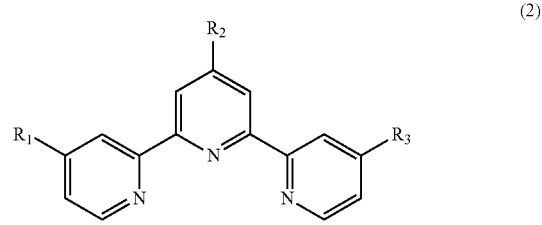

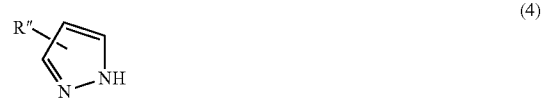

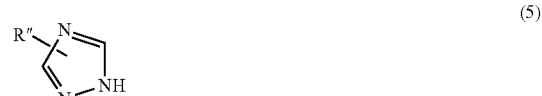

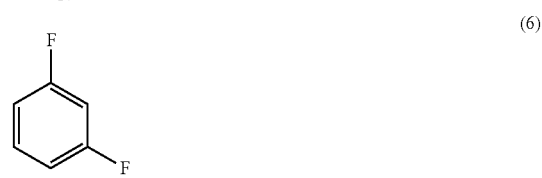

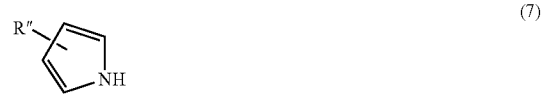

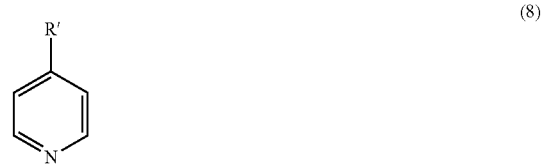

14 Claims, 2 Drawing Sheets

HETEROLEPTIC, DUAL TRIDENTATE RU(II) COMPLEXES AS SENSITIZERS FOR DYE-SENSITIZED SOLAR CELLS

BACKGROUND OF THE INVENTION

1. Field of the Invention

The present invention relates to solar sensitizers using heteroleptic, dual tridentate Ru(II) complexes and dye-sensitized solar cells, particularly to sensitizers and dye-sensitized solar cells with better conversion efficiency.

2. Description of the Prior Art

Petrochemical fuel is a nonrenewable energy source and might possibly run out very soon. In addition, burning petrochemical fuel results in excessive $CO_2$ exhausts which not only pollute the atmosphere, but also become one of the primary causes of global warming. Therefore, searching for alternative energy supplies to reduce reliance on petrochemical fuels is a subject of great urgency.

During the development of green energy, it is found that solar energy is the cleanest, most abundant and requires neither mining nor refinement. Solar energy, therefore, becomes the most promising technology among the current development and search for new energy. The manufacturing process of a dye-sensitized solar cell (DSSC) is simple and the associated fabrication cost is also significantly lower than that of a silicon-based solar cell of prior arts. Therefore, DSSC has been regarded as one of the most notable solar cell technologies following silicon-based solar cells. Because the intrinsic properties of photosensitizers directly affect the photoelectric conversion efficiency of a DSSC, the photosensitizers therefore becomes one of key issues while conducting research on DSSCs.

A N719 dye and black dye (N749 dye) are photosensitizers commonly used at present, which comprises the structure shown in following formulae. However, the conventional N719 and N749 dyes possess two and three monodentate $NCS^-$ (thiocyanate) ligands, which are considered to be the weakest coordination ligands of the whole molecule, and can be easily replaced by other donor fragments in the electrolyte solution of DSSCs. Therefore, replacing $NCS^-$ ligands with other stronger coordinated chelates or chromophoric ligands would allow significant increase of efficiency and life-expectancy of DSSCs.

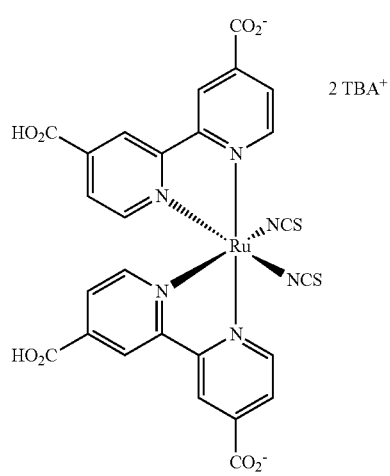

N719

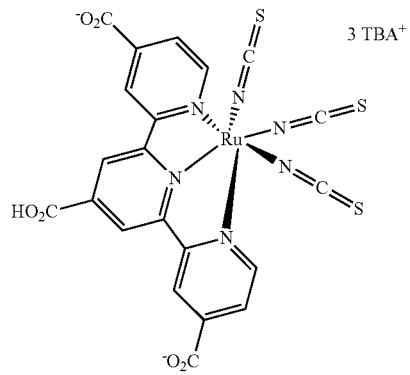

N749

To sum up the foregoing descriptions, the photoelectric conversion efficiency of a DSSC is directly dependent on the inherent property of photosensitizer; therefore, developing photosensitizers with decent photoelectric conversion efficiency is an important goal to be achieved.

SUMMARY OF THE INVENTION

The present invention is directed to the design and preparation of photosensitizers having double-negative charged, tridentate ligands in substitution of three thiocyanates as observed in N749 for providing higher stability and better photoelectric conversion efficiency.

According to an embodiment, photosensitizers having a formula of $RuL_1L_2$ (1) are provided, wherein Ru is ruthenium; $L_1$ and $L_2$ are heterocyclic tridentate ligands. $L_1$ has a formula of (2),

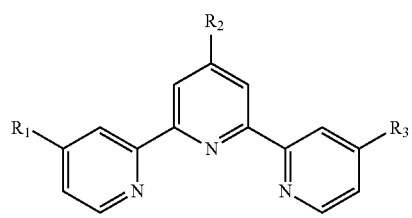

(2)

and $L_2$ has a formula of $G_1G_2G_3$ (3), wherein $G_1$ and $G_3$ are selected from the group consisting of formulae (4) to (7), and $G_2$ is selected from the group consisting of formulae (7) and (8).

(4)

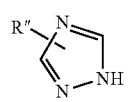

(5)

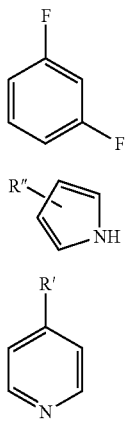

(6)

(7)

(8)

Each of $R_1$ to $R_3$ in $L_1$ is a member independently selected from the group consisting of hydrogen, a carboxyl group, a salt of a carboxyl group, a sulfonic acid group, a salt of a sulfonic acid group, a phosphoric acid group and a salt of a phosphoric acid group. Each of R' and R'' in $L_2$ is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

The present invention is also directed to the fabrication of dye-sensitized solar cells, which have better photoelectric conversion efficiency and improved device efficiency and longer life-expectancy for DSSCs.

According to another embodiment, a DSSC comprises a first electrode (photoanode), a second electrode (cathode) and an electrolyte. The first electrode comprises a transparent conductive substrate and a porous membrane, wherein the porous membrane, disposed on a surface of the transparent conductive substrate, comprises a semiconductor material and is loaded with the aforementioned photosensitizers. The electrolyte is disposed between the porous membrane and the second electrode.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein.

DESCRIPTION OF THE PREFERRED EMBODIMENT

Figure 1:
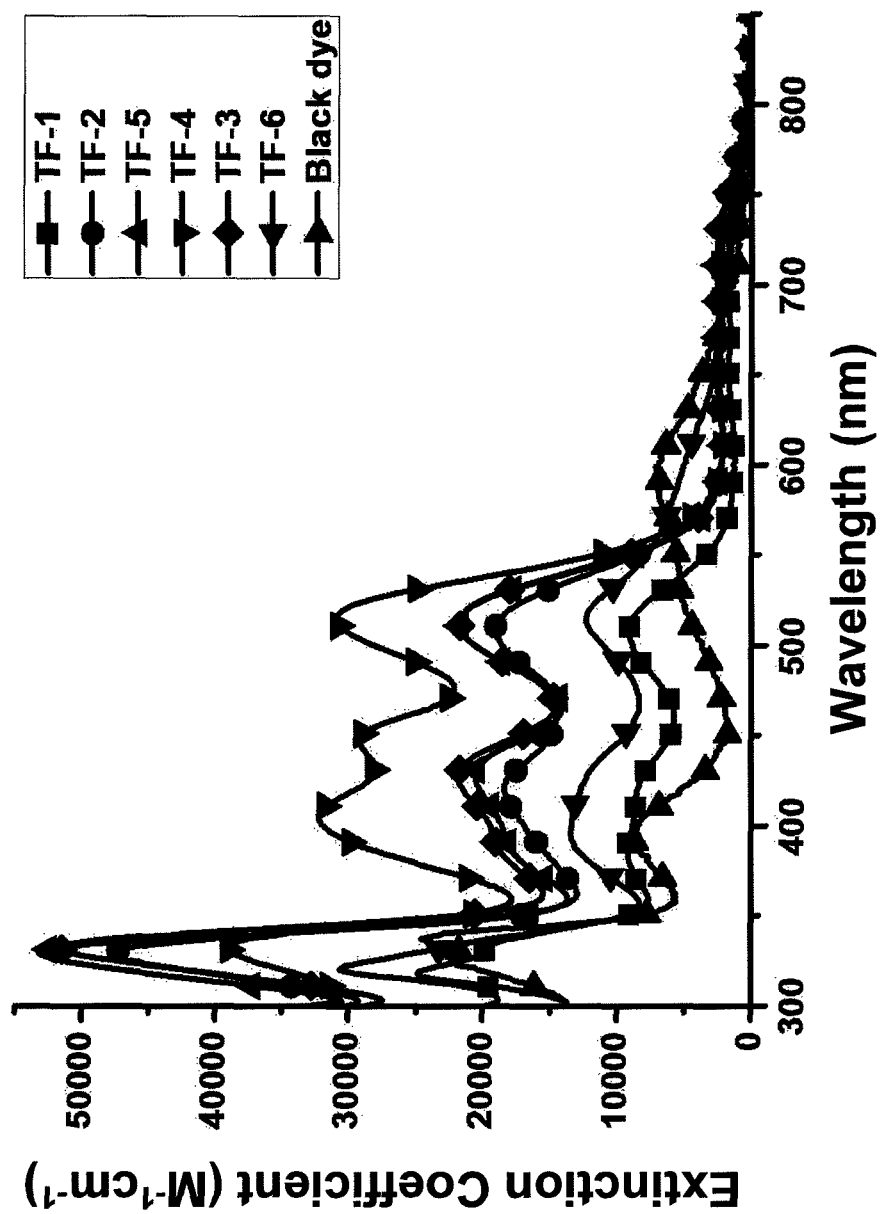
FIG. 1 is a diagram illustrating absorption spectra of photosensitizers according to one preferred embodiment of the present invention and the conventional dye.

Photosensitizers having a formula (1) are provided according to one embodiment of the present invention:

$$RuL_1L_2 \quad (1)$$

wherein Ru is ruthenium; $L_1$ and $L_2$ are heterocyclic tridentate ligands. $L_1$ is a 2,2';6',2''-terpyridine compound and has a formula of (2):

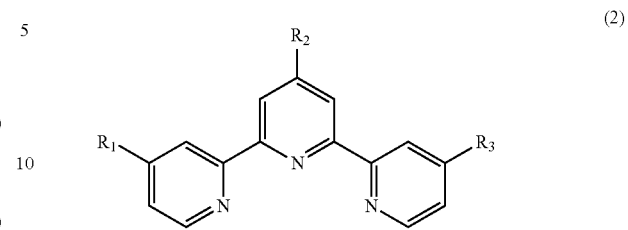

(2)

wherein $R_1$-$R_3$ is selected from the group consisting of hydrogen, a carboxyl group, a salt of a carboxyl group, a sulfonic acid group, a salt of a sulfonic acid group, a phosphoric acid group and a salt of a phosphoric acid group. The cation corresponding to the carboxylate, sulfonate and phosphate includes without limitation to an ammonium ion, a metal ion (such as alkali metal ion) and so on. For example, $L_1$ is represented by the following formulae:

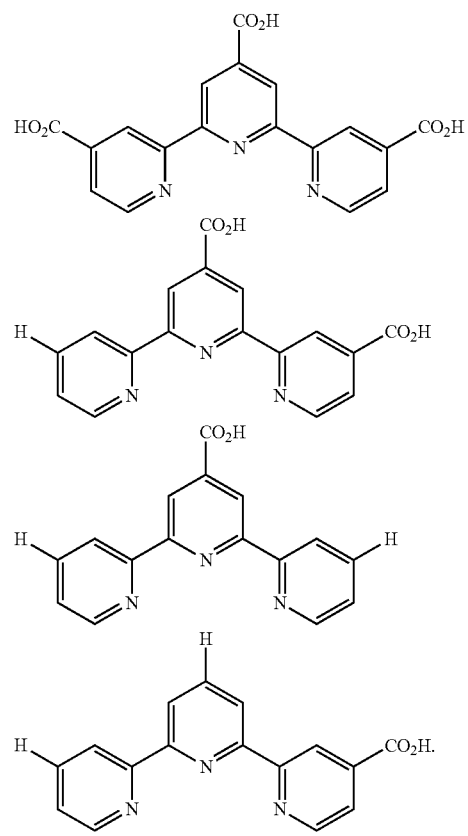

Preferably, $L_1$ is 4,4',4''-tricarboxy-2,2';6',2''-terpyridine. $L_2$ has a formula (3):

$$G_1G_2G_3 \quad (3)$$

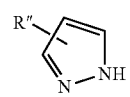

(4)

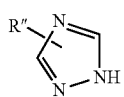

(5)

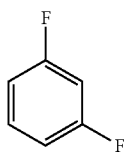

(6)

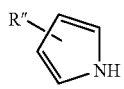

(7)

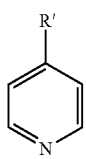

(8)

wherein $G_1$ and $G_3$ are selected from the group consisting of formulae (4) to (7), and $G_2$ is selected from the group consisting of formulae (7) and (8).

For example, $L_2$ is presented by formulae (9) to (14):

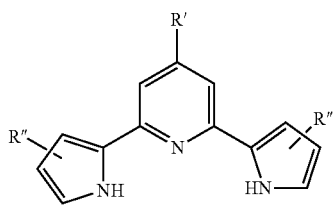

(9)

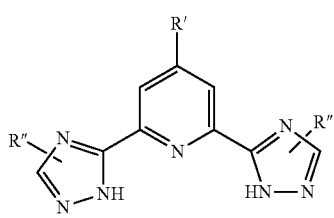

(10)

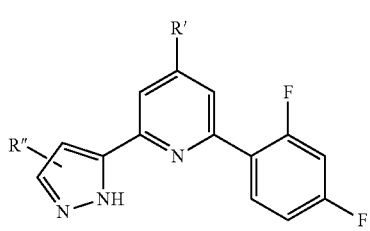

(11)

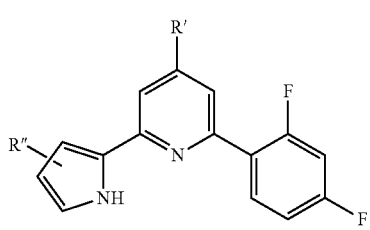

(12)

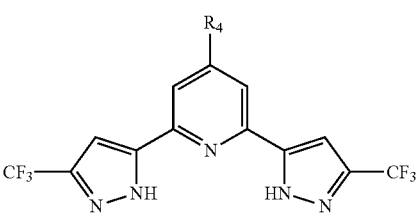

(13)

(14)

wherein each of R' and R" in $L_2$ is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Preferably, $L_2$ is presented by formula (15) or (16):

(15)

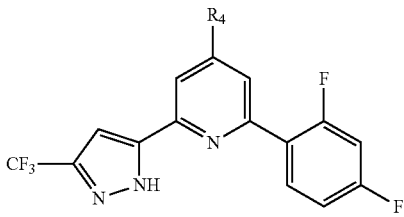

wherein R₄ is selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

In one preferred embodiment, R₄ includes an aryl group or a heteroaryl group and is selected from the group consisting of thiophene, 5-(thiophen-2-yl)thiophene, thiophene-substituted $C_1$-$C_{20}$ alkyl, 5-(thiophen-2-yl)thiophene-substituted $C_1$-$C_{20}$ alkyl, 1-tert-butyl-4-[(1E)-prop-1-en-1-yl]benzene and N,N-diphenylaniline.

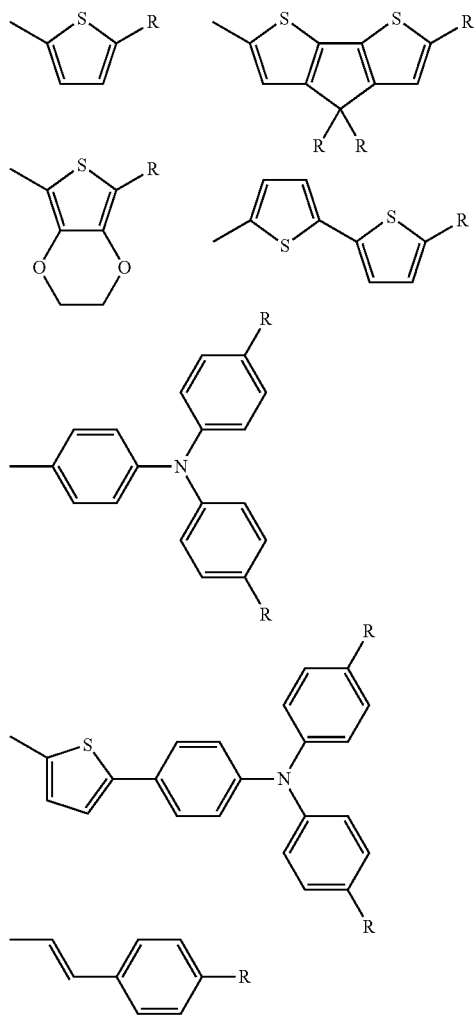

Herein, R is selected form the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

EXAMPLE LIGANDS

The synthesis method and spectrum data for example ligand 1 having the tridentate ligand $L_2$ and represented by the formula (15), where R₄=H, is provided as following.

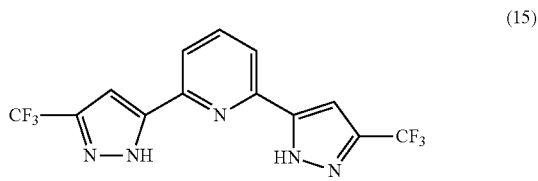 [SMILES: FC(F)(F)c1cc(-c2cccc(-c3cc(C(F)(F)F)n[nH]3)n2)[nH]n1]

To a stirred suspension of NaOEt (1.25 g, 18.4 mmol) and THF (40 mL) at 0° C., a 30 mL THF solution of 2,6-diacetylpyridine (1 g, 6.1 mmol) and ethyl trifluoroacetate (2.18 mL, 18.4 mmol) were added in sequence. The mixture was heated at 80° C. for 12 h and then was neutralized with 2 M HCl until pH=5-6. After evaporating of THF, the residue was extracted with $CH_2Cl_2$ (3×80 mL). The combined extracts were washed with water, dried over anhydrous $Na_2SO_4$, and concentrated under vacuum to give the corresponding β-diketone compound. Without further purification, hydrazine monohydrate (98%, 2.9 mL, 59.9 mmol) was added into a 50 mL of EtOH solution of the aforementioned β-diketone reagent. The solution was reflux for 12 h and then the solvent was evaporated. The residue was redissolved in $CH_2Cl_2$ (100 mL), and the solution was washed with water, dried over anhydrous $MgSO_4$, and concentrated. Finally, the product was purified by silica gel column chromatography using a 3:1 mixture of hexane and ethyl acetate, giving the desired tridentate ligand as a white solid. Yield: 0.86 g, 40%.

Spectral data for formula (15): MS (EI), m/z 347 (M)⁺. ¹H NMR (400 MHz, d-acetone, 298K): δ 13.68 (s, 2H), 8.08 (t, $J_{HH}$=8 Hz, 1H), 7.96 (d, $J_{HH}$=8 Hz, 2H), 7.40 (s, 2H).

The synthesis method and spectrum data for example ligand 2 having the tridentate ligand $L_2$ and represented by the formula (16), where R₄=H, is provided as following.

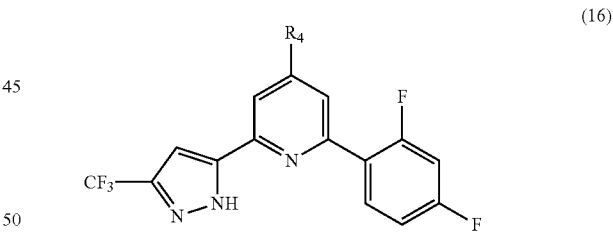

To a stirred suspension of NaOEt (0.77 g, 10.4 mmol) and THF (40 mL) at 0° C., a 30 mL THF solution of 1-(6-(2,4-difluorophenyl)pyridin-2-yl)ethanone (300 mg, 1.3 mmol) and ethyl trifluoroacetate (0.3 mL, 1.9 mmol) were added in sequence. The mixture was heated at 80° C. for 6 h and then was neutralized with 2 M HCl until pH=3. After evaporating of THF, the residue was extracted with $CH_2Cl_2$ (3×80 mL). The combined extracts were washed with water and concentrated under vacuum to give the corresponding β-diketone compound. Without further purification, hydrazine monohydrate (about 5 equiv.) was added into a 50 mL of EtOH solution of the aforementioned β-diketone reagent. The solution was reflux for 12 h and then the solvent was evaporated. The residue was redissolved in $CH_2Cl_2$ (100 mL), and the solution was washed with water, dried over anhydrous $MgSO_4$, and concentrated. Finally, the product was purified by silica gel column chromatography using a 3:1 mixture of hexane and ethyl acetate, giving the desired tridentate ligand as a white solid. Yield: 0.30 g, 72%.

Spectral data for formula (16): $^1$H NMR (CDCl$_3$, 400 MHz, 298K): δ 11.40 (s, 1H), 8.00 (q, J$_{HH}$=8.4 Hz, 1H), 7.85 (t, J$_{HH}$=8.0 Hz, 1H), 7.73 (d, J$_{HH}$=8.4 Hz, 1H), 7.56 (d, J$_{HH}$=8.0 Hz, 1H), 7.03 (t, J$_{HH}$=8.0 Hz, 1H), 6.97 (s, 1H), 6.93 (t, J$_{HH}$=8.0 Hz, 1H).

Example Ru(II) Complexes

In one embodiment, the Ru complex of the present invention is represented as formula (17).

(17)

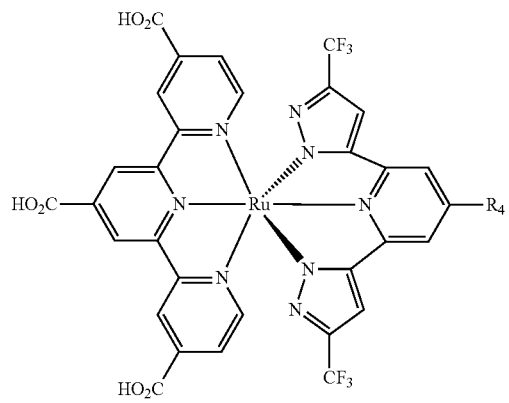

A mixture of 2,6-bis(3-trifluoromethyl-1H-pyrazol-5-yl) pyridine (53 mg, 0.15 mmol), Ru(tectpy)Cl$_3$ (100 mg, 0.15 mmol) and 4-ethylmorpholine (0.05 mL, 0.39 mmol) in 30 mL of ethanol was heated at 80° C. for 3 h. After evaporating the solvent, the aqueous phase was separated and the residue was extracted with CH$_2$Cl$_2$ (3×25 mL). The crude product was purified by silica gel column chromatography (hexane/ ethyl acetate=1:1). After then, this solid was dissolved in a mixture of acetone (30 mL) and 1.5 M NaOH solution (1.8 mL). The solution was heated to 60° C. under N2 for 3 h. Finally, the solvent was removed, the solid was dissolved in 10 mL of H$_2$O and was titrated with 2 N HCl to pH 3 to afford a black precipitate. This black product was washed with CH$_2$Cl$_2$ and acetone, to yield the compound of formula (17).

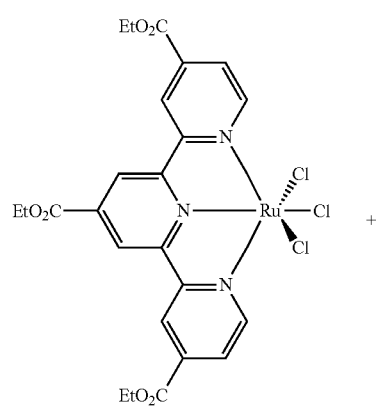

+

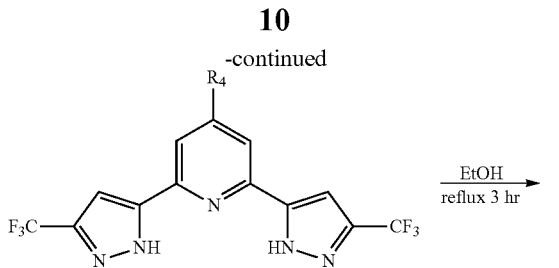

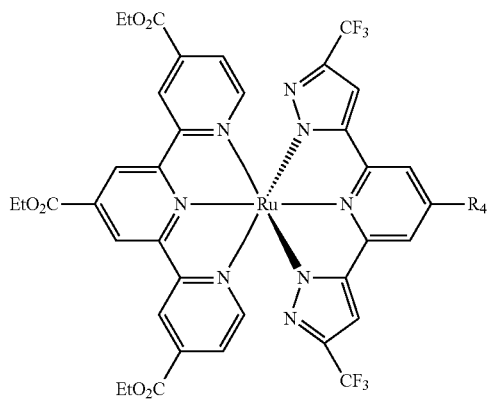

+

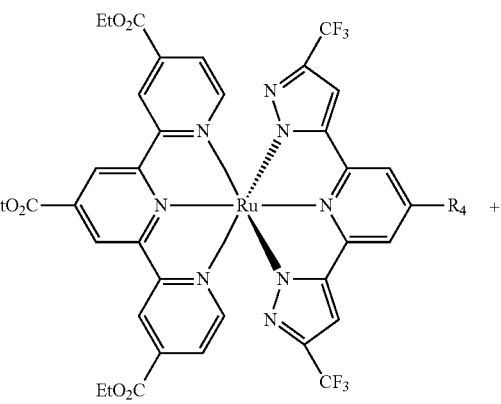

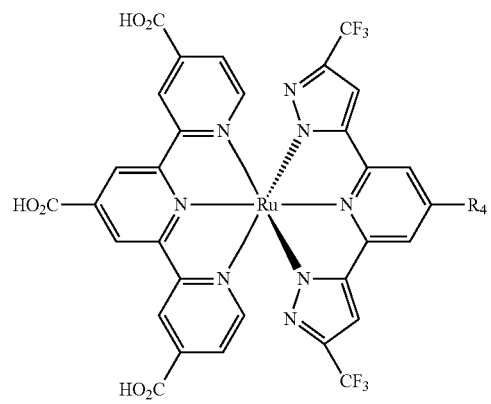

Example 1

TF-1

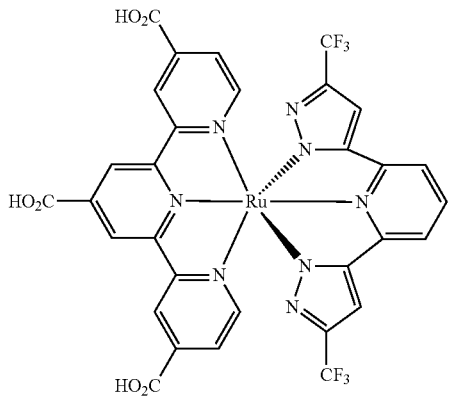

TF-1 is an example compound of formula (17), where $R_4$=H and was prepared according to the afore-mentioned procedure. Yield: 78% (60 mg, 0.07 mmol).

Spectrum Data of TF-1:
MS (FAB, $^{102}$Ru): m/z 812 (M+1)$^+$. $^1$H NMR (400 MHz, d$_6$-DMSO, 298K): δ 9.37 (s, 2H), 9.14 (s, 2H), 8.17 (t, $J_{HH}$=8.0 Hz, 1H), 8.06 (d, $J_{HH}$=8.0 Hz, 2H), 7.70 (d, $J_{HH}$=5.6 Hz, 2H), 7.59 (d, $J_{HH}$=5.6 Hz, 2H), 7.19 (s, 2H); $^{19}$F NMR (376 MHz, d$_6$-DMSO, 298K): δ −58.44 (s, 3F; CF$_3$).

Anal. Calcd. for $C_{31}H_{16}F_6N_8O_6Ru·3H_2O$: C, 43.01; N, 12.94; H, 2.56. Found: C, 43.22; N, 12.71; H, 2.51.

Example 2

TF-2

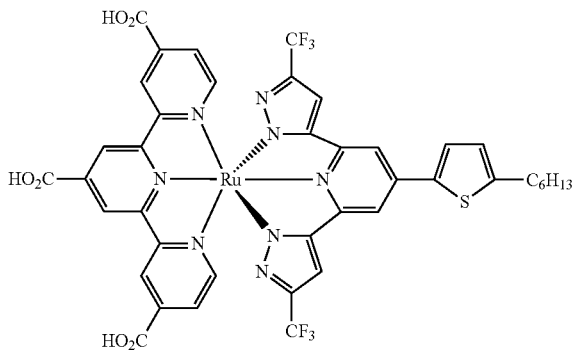

TF-2 is another example compound of formula (17), where $R_4$=2-hexylthiophene and was prepared according to the fore-mentioned procedure. Yield: 87% (264 mg, 0.27 mmol).

Spectral Data of TF-2:
MS (FAB, $^{102}$Ru) m/z 978 (M+1)$^+$. $^1$H NMR (400 MHz, d$_6$-DMSO, 298K): δ 9.36 (s, 2H), 9.14 (s, 2H), 8.34 (s, 2H), 7.96 (d, $J_{HH}$=4 Hz, 1H), 7.71~7.67 (m, 4H), 7.33 (s, 2H), 7.10 (d, $J_{HH}$=4 Hz, 1H), 2.95 (t, $J_{HH}$=8 Hz, 2H), 1.74 (quin, $J_{HH}$=8 Hz, 2H), 1.41~1.31 (m, 6H), 0.98 (t, $J_{HH}$=8 Hz, 3H). $^{19}$F NMR (376 MHz, d$_6$-DMSO, 298K): δ −58.52 (s, 6F). Anal. Calcd. for $C_{41}H_{32}F_6N_8O_7RuS·H_2O$: C, 49.45; N, 11.25; H, 3.24. Found: C, 49.39; N, 11.14; H, 3.59.

Example 3

TF-3

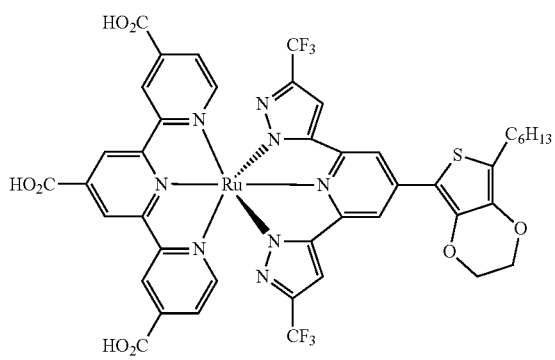

TF-3 is another example compound of formula (17), where $R_4$=5-hexyl-2H,3H-thieno[3,4-b][1,4]dioxine and was prepared according to the fore-mentioned procedure. Yield: 86% (48 mg, 0.05 mmol).

Spectral Data of TF-3:
MS (FAB, $^{102}$Ru): m/z 1036 (M+1)$^+$. $^1$H NMR (400 MHz, d$_6$-DMSO, 298K): δ 9.36 (s, 2H), 9.13 (s, 2H), 8.21 (s, 2H), 7.71~7.67 (m, 4H), 7.26 (s, 2H), 4.52 (t, $J_{HH}$=4 Hz, 2H), 4.38 (t, $J_{HH}$=4 Hz, 2H), 2.76 (t, $J_{HH}$=8 Hz, 2H), 1.66 (quin, $J_{HH}$=8 Hz, 2H), 1.40~1.31 (m, 6H), 0.89 (t, $J_{HH}$=8 Hz, 3H). $^{19}$F NMR (376 MHz, d$_6$-DMSO, 298K): δ −58.41 (s, 6F).

Example 4

TF-4

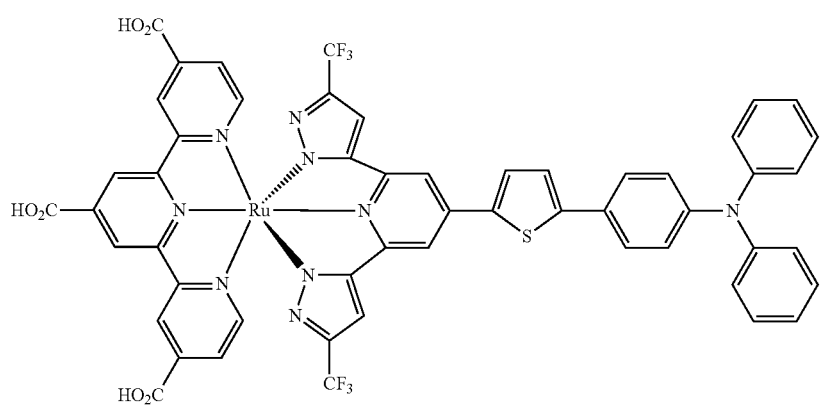

TF-4 is another example compound of formula (17), where R$_4$=N,N-diphenyl-4-(thiophen-2-yl)aniline and was prepared according to the fore-mentioned procedure. Yield: 51% (26 mg, 0.02 mmol).

Spectral Data of TF-4:

MS (FAB, $^{102}$Ru): m/z 1137 (M+1)$^+$. $^1$H NMR (400 MHz, d$_6$-DMSO, 298K): δ 9.36 (s, 2H), 9.14 (s, 2H), 8.43 (s, 2H), 8.14 (d, J$_{HH}$=4 Hz, 1H), 7.73~7.69 (m, 7H), 7.38~7.34 (m, 6H), 7.13~7.05 (m, 8H). $^{19}$F NMR (376 MHz, d$_6$-DMSO, 298K): δ −58.47 (s, 6F).

Example 5

TF-5

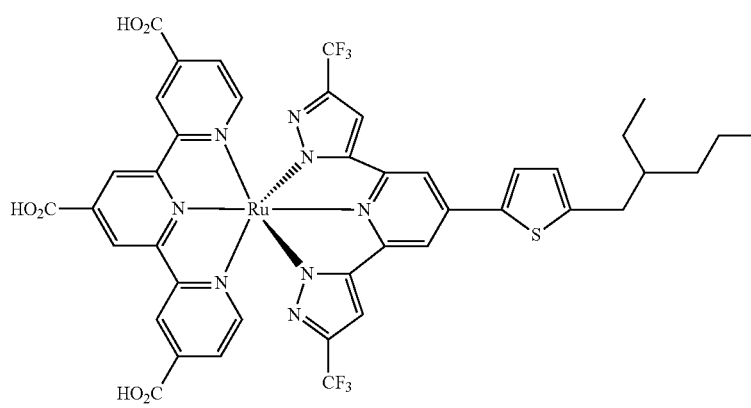

TF-5 is another example compound of formula (17), where R$_4$=2-(2-ethylhexyl)thiophene and was prepared according to the fore-mentioned procedure. Yield: 75% (62 mg, 0.06 mmol).

Spectral Data of TF-5:

MS (FAB, $^{102}$Ru): m/z 1006 (M+1)$^+$. $^1$H NMR (400 MHz, d$_6$-DMSO, 298K): δ 9.32 (s, 2H), 9.13 (s, 2H), 8.36 (s, 2H), 7.97 (d, J$_{HH}$=4.0 Hz, 1H), 7.72~7.69 (m, 4H), 7.35 (s, 2H), 7.09 (d, J$_{HH}$=4.0 Hz, 1H), 2.89 (d, J$_{HH}$=8.0 Hz, 2H), 1.67 (s, 1H), 1.41~1.30 (m, 8H), 0.95~0.88 (m, 6H); $^{19}$F NMR (376 MHz, d$_6$-DMSO, 298K): δ −58.43 (s, 3F; CF$_3$).

Example 6

TF-6

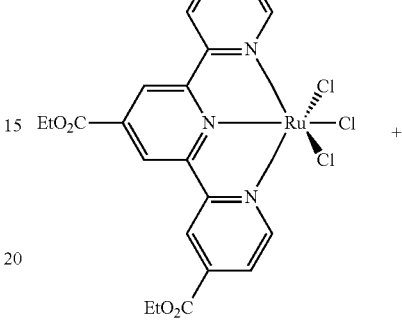

-continued

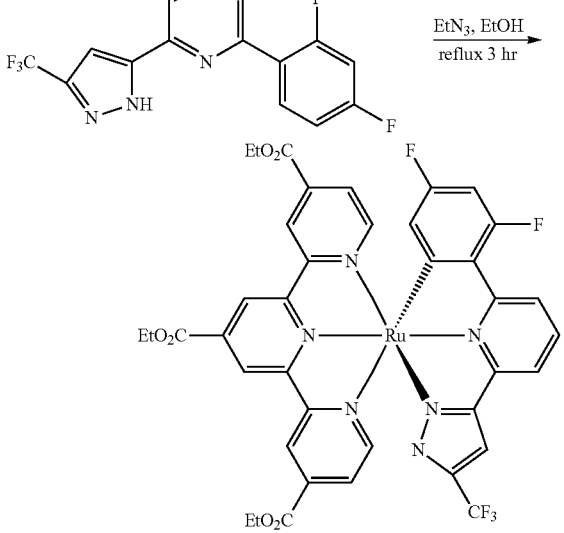

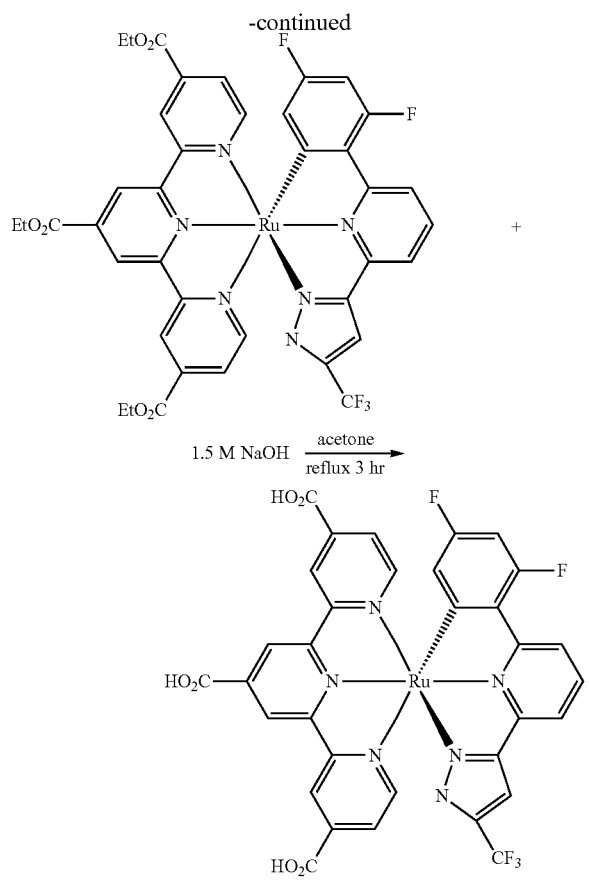

A mixture of (2-(2,4-Difluorophenyl)-6-(3-(trifluoromethyl)-1H-pyrazol-5-yl)pyridine) (21 mg, 0.06 mmol), Ru(tectpy)Cl$_3$ (40 mg, 0.06 mmol) and triethylamine (0.6 mL) in 25 mL of ethanol was heated at 90° C. for 3 h. After evaporating the solvent, the aqueous phase was separated and the residue was extracted with CH$_2$Cl$_2$ (3×25 mL). The crude product was purified by silica gel column chromatography (dichoromethane/ethyl acetate=10:1). After then, this solid was dissolved in a mixture of acetone (30 mL) and 1.5 M NaOH solution (1.8 mL). The solution was heated to 60° C. under N$_2$ for 3 h. Finally, the solvent was removed, the solid was dissolved in 10 mL of H$_2$O and was titrated with 2 N HCl to pH 3 to afford a black precipitate. This black product was washed with CH$_2$Cl$_2$ and ether. Yield: 24% (12 mg, 0.014 mmol), Spectral Data of TF-6:
MS (FAB, $^{102}$Ru): m/z 806 (M+1)$^+$. $^1$H NMR (d$_6$-DMSO, 400 MHz, 298K) δ:9.32 (s, 2H), 9.12 (s, 2H), 8.10 (s, 3H), 7.68 (d, J$_{HH}$=5.6 Hz, 2H), 7.62 (d, J$_{HH}$=5.2 Hz, 2H), 7.21 (s, 1H), 6.40 (t, J$_{HF}$=10.8 Hz, 1H), 4.65 (d, J$_{HF}$=7.2 Hz, 1H).

Referring to FIG. 1, which is a diagram illustrating absorption spectra of photosensitizers of the formula (17) according to one preferred embodiment of the present invention and N749 (Black dye).

According to the spectra data illustrated in FIG. 1, the photosensitizers, TF-2, TF-3 and TF-4 have better extinction coefficient in the range between 350 nm and 550 nm in comparison to N749.

Figure 2:
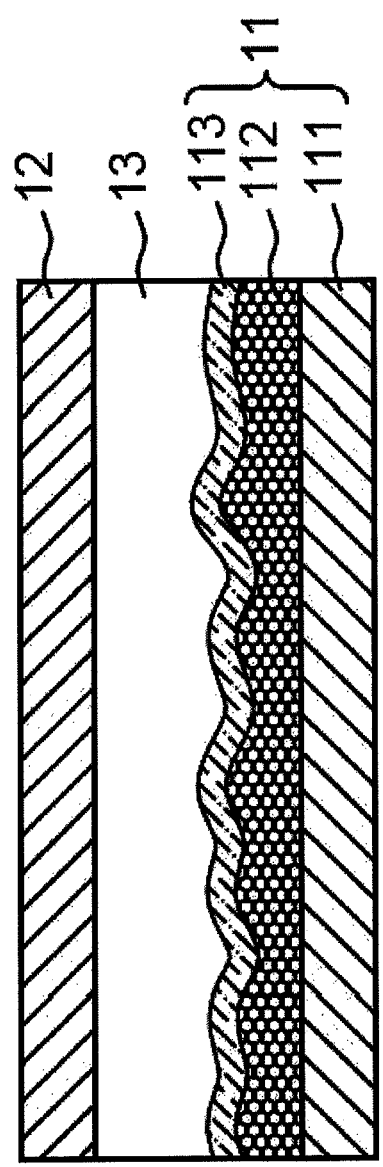
FIG. 2 is a schematic diagram illustrating the structure of a dye-sensitized solar cell according to one embodiment of the present invention.

Referring to FIG. 2, a DSSC of an embodiment of the present invention comprises a first electrode 11 (photoanode), a second electrode 12 (cathode) and an electrolyte 13. The first electrode 11 comprises a transparent conductive substrate 111 and a porous membrane 112. The porous membrane 112, disposed on a surface of the transparent conductive substrate 111, is loaded with the aforementioned photosensitizers 113. The porous membrane 112 comprises a semiconductor material, such as TiO$_2$. In one embodiment, the transparent conductive substrate 111 comprises F-doped SnO$_2$ glass (FTO glass). The electrolyte 13 is disposed between the porous membrane 112 and the second electrode 12. The structures of the photosensitizers 113 are identical with the aforementioned photosensitizers; therefore, the detail description is omitted here.

The aforementioned photosensitizers TF-1~TF-6 are utilized to produce a DSSC of the present invention. The properties of DSSCs are illustrated in table 1, wherein the first electrode 11 comprises photosensitizers TF-1~TF-6, a porous membrane TiO$_2$ and FTO glass; the second electrode 12 comprises a Pt electrode, such as a general glass doped with metal Pt and other transparent conductive materials, e.g. carbon black or graphite; the electrolyte comprises a mixture consisting of 0.6 M 1,2-dimethyl-3-propylimidazolium iodide (DMPII), 0.1M Lithium iodide (LiI), 0.1M I$_2$, and 0.5 M tert-butylpyridine in acetonitrile.

TABLE 1

| Dye | $V_{OC}$, V | $J_{SC}$, mA·cm$^{-2}$ | FF | η, % |
|---|---|---|---|---|
| TF-1 | 740 | 18.22 | 0.676 | 9.11 |
| TF-2 | 790 | 20.00 | 0.665 | 10.51 |
| TF-3 | 760 | 21.39 | 0.660 | 10.72 |
| TF-4 | 770 | 20.27 | 0.675 | 10.55 |
| TF-5 | 740 | 20.36 | 0.650 | 9.81 |
| TF-6 | 770 | 10.17 | 0.692 | 5.42 |
| N749 | 720 | 19.49 | 0.657 | 9.22 |

The DSSCs of the present invention have better photoelectric conversion efficiency as illustrated in Table 1. To be specific, the DSSCs of the present invention including photosensitizers TF-2, TF-3 and TF-4 respectively have better η of 10.51%, 10.72% and 10.55% than that of N749 (η=9.22%).

In addition, photosensitizers TF-2, TF-3, TF-4 and TF-5 are more efficient than N719, as confirmed by the better performance data such as higher efficiencies, including better $V_{OC}$ and $J_{SC}$ characteristics. In other words, the DSSCs of the present invention may include the first electrode prepared with the much thinner nanoporous TiO$_2$ layer so as to prevent the unnecessary reduction of $V_{OC}$. It has been reported that the $V_{OC}$ is inversely proportional to the back recombination of injected electrons with the oxidized dye molecule or components in electrolyte. Moreover, usage of fewer amounts of photosensitizers can also reduce the overall cost of DSSC fabrication.

To sum up, the photosensitizers of the present invention, including heterocyclic tridentate ligands, are thiocyanate-free and have better photoelectric conversion efficiency η than devices fabricated employing the traditional N749 dye. Therefore, the DSSCs prepared with the photosensitizers of the present invention may provide better performance in overall battery efficiency.

While the invention can be subject to various modifications and alternative forms, a specific example thereof has been shown in the drawings and is herein described in detail. It should be understood, however, that the invention is not intended to be limited to the particular form disclosed, but on the contrary, the invention is intended to cover all modifications, equivalents, and alternatives falling within the spirit and scope of the appended claims.

What is claimed is:

1. A heteroleptic, dual tridentate Ru(II) complex having a formula of (1):

$$RuL_1L_2 \quad (1),$$

wherein Ru is ruthenium, $L_1$ and $L_2$ are heterocyclic tridentate ligands;

$L_1$ has a formula of (2):

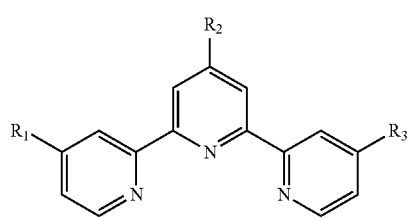
(2)

$L_2$ has a formula of (3):

$$G_1G_2G_3 \quad (3),$$

wherein $G_1$ and $G_3$ are selected from the group consisting of formulae (4) to (7), and $G_2$ is selected from the group consisting of formulae (7) and (8);

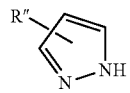
(4)

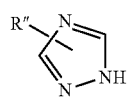
(5)

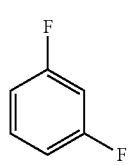
(6)

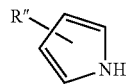
(7)

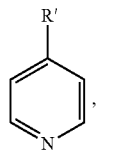
(8)

wherein each of $R_1$ to $R_3$ in $L_1$ is a member independently selected from the group consisting of hydrogen, a carboxyl group, a salt of a carboxyl group, a sulfonic acid group, a salt of a sulfonic acid group, a phosphoric acid group and a salt of a phosphoric acid group; and each of R' and R'' in $L_2$ is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

2. The heteroleptic, dual tridentate Ru(II) complex as claimed in claim 1, wherein $L_1$ is 4,4',4''-tricarboxy-2,2';6',2''-terpyridine.

3. The heteroleptic, dual tridentate Ru(II) complex as claimed in claim 1, wherein $L_2$ is selected from the group consisting of formulae (9) to (14):

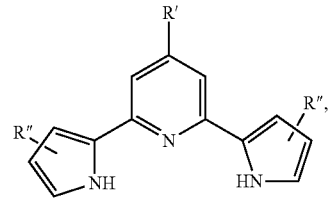
(9)

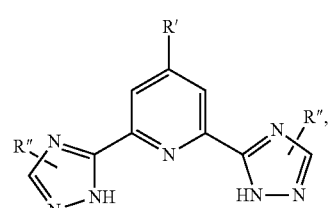
(10)

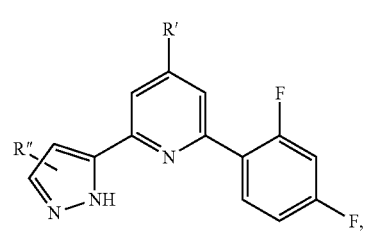
(11)

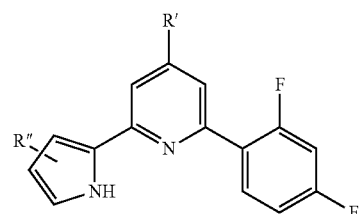
(12)

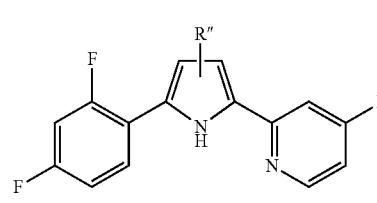
(13)

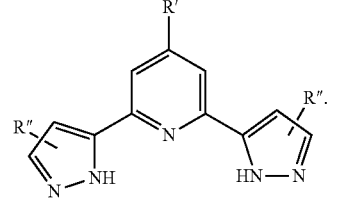
(14)

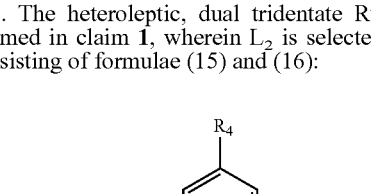

4. The heteroleptic, dual tridentate Ru(II) complex as claimed in claim 1, wherein $L_2$ is selected from the group consisting of formulae (15) and (16):

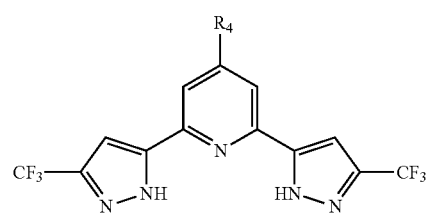
(15)

-continued (16)

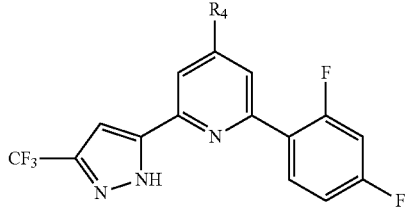

wherein R₄ is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

5. The heteroleptic, dual tridentate Ru(II) complex as claimed in claim 4, wherein R₄ is heteroaryl or aryl.

6. The heteroleptic, dual tridentate Ru(II) complex as claimed in claim 5, wherein R₄ is selected from the group consisting of following formulae:

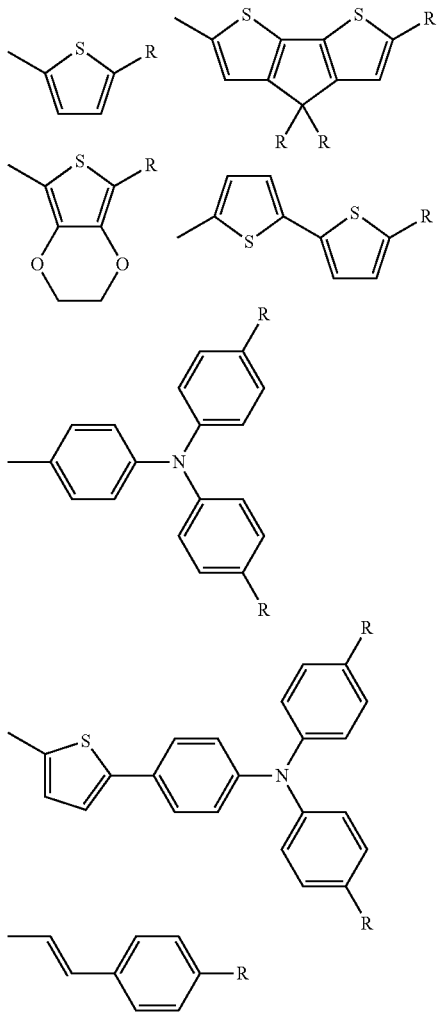

wherein R is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

7. A dye-sensitized solar cell comprising:
  a first electrode comprising:
    a transparent conductive substrate; and
    a porous membrane comprising a semiconductor material, disposed on a surface of said transparent conductive substrate, and loaded with photosensitizers;
  a second electrode; and
  an electrolyte, disposed between said porous membrane and said second electrode, wherein said photosensitizers comprising a chemical formula represented by formula of (1):

$$RuL_1L_2 \quad (1)$$

wherein Ru is ruthenium, $L_1$ and $L_2$ are heterocyclic tridentate ligands;
$L_1$ has a formula of (2)

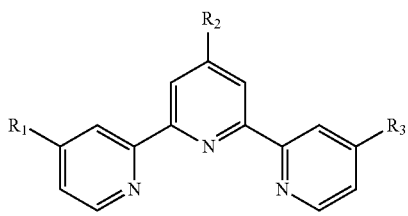

(2)

$L_2$ has a formula of (3)

$$G_1G_2G_3 \quad (3)$$

wherein $G_1$ and $G_3$ are selected from the group consisting of formula (4) to (7), and $G_2$ is selected from the group consisting of formula (7) and (8);

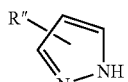

(4)

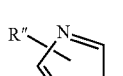

(5)

(6)

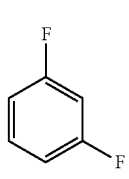

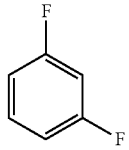

(7)

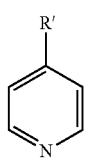

(8)

wherein each of $R_1$ to $R_3$ in $L_1$ is a member independently selected from the group consisting of hydrogen, a carboxyl group, a salt of a carboxyl group, a sulfonic acid group, a salt of a sulfonic acid group, a phosphoric acid group and a salt of a phosphoric acid group; and
each of R' and R" in $L_2$ is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

8. The dye-sensitized solar cell as claimed in claim 7, wherein $L_1$ is 4,4',4"-tricarboxy-2,2';6',2"-terpyridine.

9. The dye-sensitized solar cell as claimed in claim 7, wherein $L_2$ is selected from the group consisting of formulae (9) to (14):

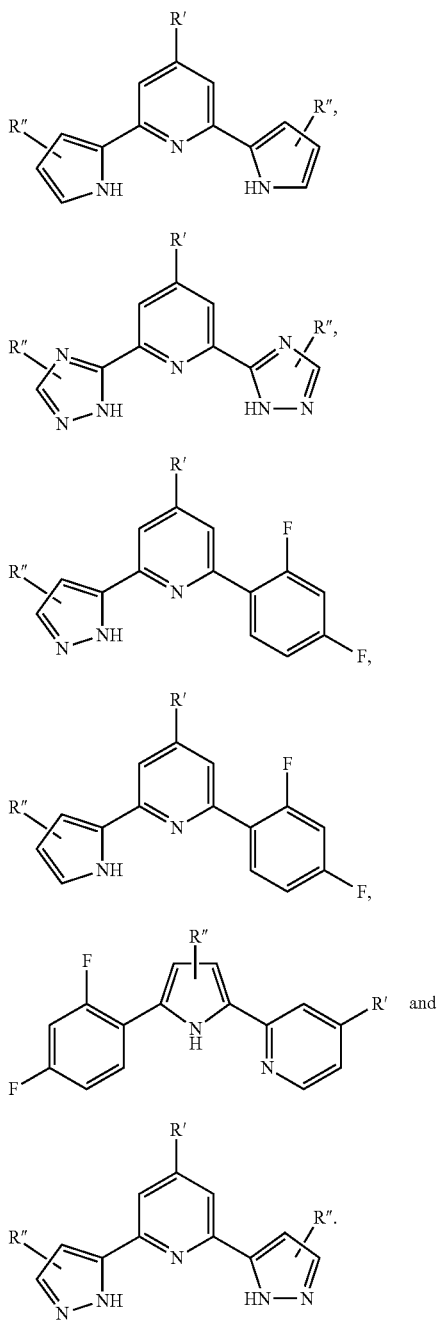

10. The dye-sensitized solar cell as claimed in claim 7, wherein $L_2$ is selected from the group consisting of formulae (15) and (16):

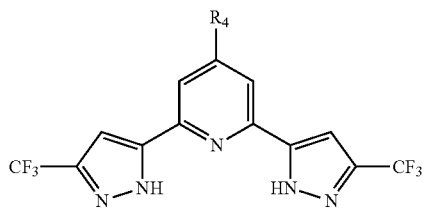

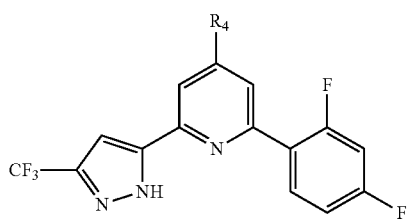

wherein $R_4$ is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

11. The dye-sensitized solar cell as claimed in claim 10, wherein $R_4$ is heteroaryl or aryl.

12. The dye-sensitized solar cell as claimed in claim 11, wherein $R_4$ is selected from the group consisting of following formulae:

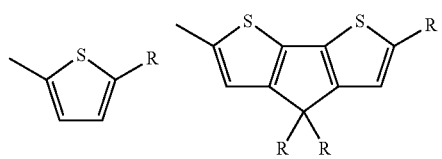

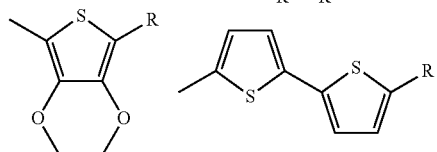

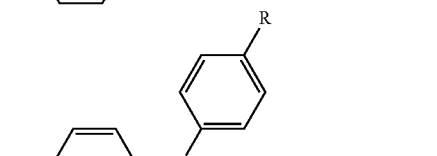

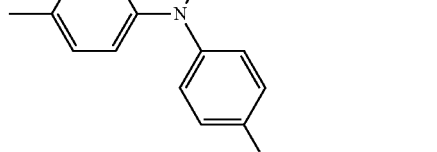

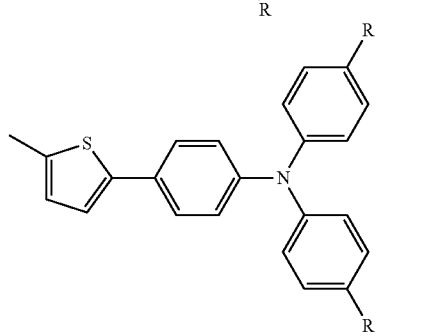

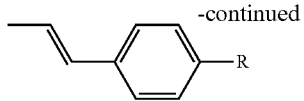

wherein R is a member independently selected from the group consisting of H, halo, cyano, trifluoromethyl, $C_2$-$C_{10}$ fluorinated alkyl group, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

13. The dye-sensitized solar cell as claimed in claim 7, wherein the material of said semiconductor comprises $TiO_2$.

14. The dye-sensitized solar cell as claimed in claim 7, wherein said transparent conductive substrate comprises FTO glass.

* * * * *